(12) United States Patent
Lahtinen et al.

(10) Patent No.: US 9,295,267 B2
(45) Date of Patent: Mar. 29, 2016

(54) BEVERAGE LOWERING SERUM CHOLESTEROL

(75) Inventors: Ritva Lahtinen, Raisio (FI); Paivi Kuusisto, Raisio (FI); Leena Koponen, Raisio (FI)

(73) Assignee: RAISIO NUTRITION LTD, Raisio (FI)

( * ) Notice: Subject to any disclaimer, the term of this patent is extended or adjusted under 35 U.S.C. 154(b) by 1025 days.

(21) Appl. No.: 13/146,282

(22) PCT Filed: Jan. 26, 2010

(86) PCT No.: PCT/FI2010/000005
§ 371 (c)(1),
(2), (4) Date: Jul. 26, 2011

(87) PCT Pub. No.: WO2010/084240
PCT Pub. Date: Jul. 29, 2010

(65) Prior Publication Data
US 2011/0288018 A1    Nov. 24, 2011

(30) Foreign Application Priority Data
Jan. 26, 2009    (FI) .................................... 2009/0023

(51) Int. Cl.
| | |
|---|---|
| *A23L 2/02* | (2006.01) |
| *A23C 9/13* | (2006.01) |
| *A23C 9/137* | (2006.01) |
| *A23C 9/152* | (2006.01) |
| *A23C 9/154* | (2006.01) |
| *A23C 11/10* | (2006.01) |
| *A23L 1/30* | (2006.01) |
| *A23L 2/52* | (2006.01) |

(52) U.S. Cl.
CPC . *A23C 9/13* (2013.01); *A23C 9/137* (2013.01); *A23C 9/152* (2013.01); *A23C 9/154* (2013.01); *A23C 11/103* (2013.01); *A23C 11/106* (2013.01); *A23L 1/3002* (2013.01); *A23L 2/02* (2013.01); *A23L 2/52* (2013.01); *A23C 2240/10* (2013.01); *A23V 2002/00* (2013.01)

(58) Field of Classification Search
CPC .......................................................... A23L 2/02
USPC .................................................. 426/599, 615
See application file for complete search history.

(56) References Cited

U.S. PATENT DOCUMENTS

| | | |
|---|---|---|
| 6,174,560 B1 | 1/2001 | Miettenen et al. |
| 2007/0190220 A1 | 8/2007 | Doat et al. |

FOREIGN PATENT DOCUMENTS

| | | | |
|---|---|---|---|
| CN | 1299619 A | | 6/2001 |
| DE | 10063288 | * | 7/2002 |
| WO | 0041491 A2 | | 7/2000 |
| WO | 02082929 A1 | | 10/2002 |
| WO | 03055324 A1 | | 7/2003 |
| WO | 2004014141 A1 | | 2/2004 |
| WO | 2004093571 A1 | | 11/2004 |
| WO | 2005049037 A1 | | 6/2005 |
| WO | 2005074717 A1 | | 8/2005 |
| WO | 2007057511 A1 | | 5/2007 |
| WO | 2007071038 A2 | | 6/2007 |
| WO | 2009071737 A1 | | 6/2009 |

OTHER PUBLICATIONS

English Abstract of Hartinger, DE 10063288, issued Jul. 2002.*
International Search Report for PCT/FI2010/000005, Completed by the European Patent Office on Jun. 24, 2010, 4 Pages.
Ralet et al. Edited by Steinbuchel et al. "Polysaccharides and Polyamides in the Food Industry; Pectins", WILEY-VCH Verlag GmbH & Co. KGaA 2005, p. 351-386.
Web site http://www.finlex.fi/fi/laki/alkup/2001/20010498 retrieved Aug. 31, 2011, "Government Decree stored in forest berries and mushrooms converting amounts of fresh berries and mushrooms in equivalent amounts", Issued in Helsinki on Jun. 13, 2001, English translation attached to original all together 4 Pages.
Search Report for FI 20090023, Completed on Aug. 26, 2009, 2 Pages.

* cited by examiner

*Primary Examiner* — David Lukton
(74) *Attorney, Agent, or Firm* — Brooks Kushman P.C.

(57) ABSTRACT

A beverage including protein, plant sterol ester and/or plant stanol ester, a fruit and/or vegetable preparation, and a stabilizer.

18 Claims, No Drawings

BEVERAGE LOWERING SERUM CHOLESTEROL

CROSS-REFERENCE TO RELATED APPLICATION

This application is the U.S. national phase of PCT Appln. No. PCT/FI2010/000005 filed Jan. 26, 2010 which claims priority to Finnish application 2009/0023 filed Jan. 26, 2009, the disclosures of which are incorporated in their entirety by reference herein.

FIELD OF INVENTION

The invention relates to a beverage for lowering serum total and LDL-cholesterol levels.

BACKGROUND OF THE INVENTION

The beverage market is increasing all over the word, especially in Asia. At the same time health aspects are more and more considered by consumers. Fruit and berry beverages are increasing their market share. Berries, fruits and vegetables are recommended to be included in the daily diet. Different types of smoothies have increased their market share during the past years. Berries, fruits and vegetables are incorporated in different type of healthy in-between meal beverages.

WO 2004/014141 discloses the use of phytosterol, phytostanols and their esterified derivatives as a creaminess enhancer in food compositions such as dairy products, e.g. yoghurts or milk.

DE 100 63 288 discloses a mixed fruit, vegetable, milk and/or wine beverage containing up to 20 g/l added phytosterols. A process for producing the beverage is also disclosed, comprising adding a solution containing phytosterols and oil to a base beverage prepared from fruit, vegetables, milk or wine.

WO 2004/093571 discloses edible products with masked bitter, sour and/or astringent taste. The products comprise a sweetening agent and plant sterol ester, wherein the amount of sweetening agent is reduced compared to a regular product.

The Finnish Government Decree No. 498/2001 discloses the conversion of the amounts of preserved forest berries and mushrooms to corresponding amounts of fresh berries and mushrooms. The decree gives the conversion of juice concentrates to corresponding amounts of fresh berries.

The use of pectins has been disclosed by Ralet, M.-C. et al. Pectins, in Polysaccharides and polyamides in the food industry (ed. Steinbuchel, A. et al.) 2005, Wiley-VCH GmbH & Co. Weinham, Vol 1 pages 351-386.

WO 2003/055324 discloses a composition containing protein hydrolysate and plant sterol for improving serum lipid profile.

WO 2007/071038 discloses a composition for use in foods, beverages and nutraceuticals containing an emulsifier having a HLB value greater than 14 and one or more sterols or stanols.

WO 2005/074717 discloses a particulate composition containing a matrix of a protein or a carbohydrate, and fatty matter containing phytosterols dispersed in the matrix. The main product application is a creamer. The particulate composition may also be used in drink powders.

WO 00/41491 discloses a food product or beverage containing plant sterol and lycopene.

WO 2005/049037 discloses phytosterol dispersions made of free phytosterols e.g. in fruit juices by homogenisation.

However, there is still a need for cholesterol-lowering protein-containing beverages also containing berries, fruits or vegetables. This type of beverage is extremely valuable and nourishing. Especially, there is a need for cholesterol-lowering beverages containing berries, fruits or vegetables, and containing non-fermented protein.

In drinkable yoghurts, which contain fermented protein, there is conventionally quite a lot of sugar added to the drink; added separately or added to the fruit material, e.g. the jam which is added to the drink. Added sugar is not beneficial from a nutritional point of view and should therefore be minimised or preferably avoided.

Another drawback is that processing of drinkable yoghurts is time-consuming including the fermentation step. Also controlling the fermentation process demands resources. Drinkable yoghurts are therefore not so attractive.

In drinkable yoghurts and also conventional spoonable yoghurts the protein structure is changed as a result of the fermentation. This change will increase the viscosity of the product and therefore the addition of plant sterol ester and/or plant stanol ester is not a problem. The yoghurts will be stable and there is no creaming of the plant sterol ester and/or plant stanol ester. However, if the proteins in the beverage are non-fermented proteins the emulsifying effect of the non-fermented protein will not be high enough to emulsify the plant sterol ester and/or plant stanol ester causing separation of the plant sterol ester and/or plant stanol ester (creaming).

Creaming is therefore the main problem when adding plant sterol ester and/or plant stanol ester to protein based beverages containing fruit and/or vegetables, especially when the fruit and/or vegetables are included in higher amounts. The problem with this instability of this type of beverage has not been solved in the prior art.

BRIEF DESCRIPTION OF THE INVENTION

It has now been found that a stable beverage containing plant stanol ester and/or plant sterol ester can be prepared using a particular composition.

The beverage according to the invention includes protein, a fruit and/or vegetable preparation, plant stanol ester and/or plant sterol ester, and a stabilising agent. Preferably the beverage further contains an emulsifier.

The beverage according to the invention is preferably used as an in-between meal beverage. It is healthy, nourishing and further lowers blood total and LDL-cholesterol levels.

The protein can be derived from dairy milk, sour milk, kefir, koumiss, ayran, yoghurt, soy milk, soy milk based yoghurt, rice milk, and rice milk based yoghurt. The dairy milk, soy milk or rice milk can be used as such, they may be made from powders, isolates or concentrates, or the powders, isolates or concentrates may be added directly into the beverage according to the invention during its preparation. Preferably the protein is derived from a non-fermented source such as dairy milk, soy milk and/or rice milk, and most preferably it is dairy milk. The beverage according to the invention therefore contains non-fermented protein, preferably from milk, soy and/or rice. Preferably at least 75% by weight of the protein is non-fermented and preferably substantially all protein (at least 99% by weight of the protein) in the beverage is non-fermented. Preferably the protein is selected from the group consisting of non-fermented dairy protein, non-fermented soy protein, non-fermented rice protein, and mixtures thereof.

The beverage according to the invention is acidic due to an addition of a fruit and/or vegetable preparation, due to an addition of an organic acid, such as citric and lactic acids and/or due to fermentation of the protein source. Preferably the beverage is acidified only with a fruit and/or vegetable preparation that is sour enough to obtain a suitable taste, but more preferably organic acid is further added to obtain the wanted acidic taste. Typically the beverage is made acidic by addition of a high enough amount of a fruit and/or vegetable preparation, more typically by addition of a high enough amount of a fruit and/or vegetable preparation and at least one organic acid, and most typically no fermentation is used for producing the acidic taste.

The "fruit and/or vegetable preparation" contains fruit and/or vegetable juices, and/or fruit and/or vegetable puree, and/or fruit pulp. Non-exclusive examples of fruits (in this specification including also berries) that can be used for producing the juice, puree or pulp are orange, apple, pomegranate, go goji, grapefruit, lemon, lime, pineapple, mango, banana, peach, grape, pear, kiwi, cherry, acerola, watermelon, honeydew melon, cantaloupe, strawberry, raspberry, cranberry, blueberry, blackberry, blackcurrant, plum, papaya, guava and their mixtures. Non-exclusive examples of vegetables that can be used for producing the vegetable preparation in the form of juice or puree are carrot, tomato, maize, celery, cucumber, beets, parsley, cabbage, lettuce, spinach, cucumber, wheat grasspea, pumpkin, sauerkraut and their mixtures. If the fruit and/or vegetable preparation contains particles detectable as nonhomogeneous in the mouth it is either homogenised as such or during any stage of the preparation process of the beverage according to the invention in order to make a homogenous product. The beverage according to the invention therefore contains a fruit and/or vegetable preparation having particles of a size (volume) typically less than 100 µm. The beverage hence practically comprises particles of a size (volume) of less than 100 µm meaning that at least 90%, preferably at least 95%, most preferably at least 99% of the particles are of a size (volume) of less than 100 µm.

As often fruit and/or vegetable concentrates may be used as fruit and/or vegetable preparation the amount of natural fruit and/or vegetable may far exceed 100% by weight of the beverage. This means that the beverage is concentrated on fruit and/or vegetable.

The beverage according to the invention may e.g. contain from ⅕ to ½ of the recommended daily dose of fruits and/or vegetables; the recommended daily dose now being four or five fruits or vegetables depending on which state's recommendation is followed. The beverage therefore has a concentration of natural fruit and/or vegetable from 30 to 1000%, preferably from 40 to 750%, more preferably from 50 to 500%, still more preferably from 80 to 300%, even more preferably from 80 to 250%, and most preferably from 90 to 250% by weight of the beverage. The fruits and/or vegetables have been added via the fruit and/or vegetable preparation into the beverage.

The beverage according to the invention may alternatively be concentrated on fruit and/or vegetable, which means the beverage has a concentration of natural fruit and/or vegetable of at least 101% by weight. Typically the concentration of natural fruit and/or vegetable is from 101% to 1000%, preferably from 150% to 700%, more preferably from 170% to 500%, still more preferably from 180% to 300%, and most preferably from 190 to 250% by weight.

The beverage according to the invention may further contain buffering agents, organic acids, sweetening agents and/or calcium.

As used here, the term "plant sterol ester and/or plant stanol ester" refers to plant sterols and/or plant stanols having at least 60%, preferably at least 85%, most preferably at least 95% of the plant sterols and/or plant stanols in esterified form.

In this specification the term "plant sterols" include 4-desmethyl sterols, 4-monomethyl sterols and the term "plant stanols" include 4-desmethyl stanols, 4-monomethyl stanols. Typical 4-desmethyl sterols are sitosterol, campesterol, stigmasterol, brassicasterol, 22-dehydro-brassicasterol and δ5-avenasterol. Typical stanols are sitostanol, campestanol and their 24-epimers. The term "plant sterol and/or plant stanol" includes all possible mixtures of named sterols and/or stanols as well as any individual sterol and/or stanol.

In this invention plant sterols and/or plant stanols are esterified with a carboxylic acid or with a blend of carboxylic acids and are called "sterol ester and/or stanol ester". Examples of suitable carboxylic acids are fatty acids (2-24 carbon atoms, saturated, monounsaturated or polyunsaturated, including also special fatty acids, such as conjugated fatty acids, e.g. CLA, and EPA and DHA), di- and tricarboxylic acids and hydroxy acids, and any mixture of said acids. Preferably the plant sterols and/or plant stanols are esterified with fatty acids, most preferably with vegetable oil based fatty acids. Most preferred in beverages according to the invention are plant stanol fatty acid esters.

Plant stanol fatty acid ester and the effects thereof, as well as a suitable method for its preparation, are disclosed in U.S. Pat. No. 6,174,560. Obviously plant sterol esters can efficiently be produced by the production method disclosed in U.S. Pat. No. 6,174,560. Alternatively fatty acid esters of plant sterols and/or plant stanols can be produced by any method disclosed in the art.

Typical examples of suitable emulsifiers used in this invention include mono- and diglyceride derivatives, such as acetic, lactic, succinic and citric acid esters; sorbitan esters; polysorbates; stearoyl lactylates, such as sodium stearoyl lactylate and calcium stearoyl lactylate; diacetyl tartaric acid esters; diacetyl lactic acid esters; sugar esters; and mixtures of any of these. More representative emulsifiers according to this invention are citric acid ester, lactic acid ester and diacetyl tartaric acid ester of mono- and diglycerides, sodium stearoyl lactylate, calcium stearoyl lactylate, sucrose fatty acid esters, and mixtures thereof. Most preferable emulsifiers used in the present invention are citric acid ester, lactic acid ester and diacetyl tartaric acid ester of mono- and diglycerides and mixtures thereof.

The term "stabiliser" includes pectin, modified starch, xanthan and guar gums. Pectin is preferred as stabiliser and the most preferable stabiliser is high methoxy pectin. High methoxy pectin has a degree of esterification of at least 50%.

As used here the term "sweetening agent" includes compounds used to increase the sweetness of the product. Sweetening agents include sugars, other carbohydrate sweeteners and non-carbohydrate sweeteners. As used here the term "sweetening agent" includes e.g. the following: sucrose, glucose, fructose, sugar syrup, malt syrup, maple syrup, starch syrup, glucose syrup, high fructose corn syrup, honey, molasses, xylitol, maltitol, lactitol, sorbitol, aspartame, asesulfame-K, saccharin, cyclamates, stevia, erythritol and sucralose. "Non-carbohydrate sweeteners", also called non-calorie sweeteners, include e.g. aspartame, asesulfame-K, saccharin, cyclamates, stevia, erythritol and sucralose. The "carbohydrate sweeteners" include e.g. sucrose, glucose, fructose, sugar syrup, malt syrup, maple syrup, starch syrup, glucose syrup, high fructose corn syrup, honey, molasses, xylitol, maltitol, lactitol and sorbitol.

DETAILED DESCRIPTION OF THE INVENTION

The present invention therefore relates to a beverage comprising protein, plant sterol ester and/or plant stanol ester, a fruit and/or vegetable preparation, and a stabiliser. Preferably the beverage further comprises an emulsifier.

The amount of plant sterol ester and/or plant stanol ester is preferably from 0.5 to 7.0%, more preferably from 0.6 to 5.0%, still more preferably from 0.7 to 4.0%, and most preferably from 1.0 to 4.0% by weight of the beverage.

The protein comprises at least 75% by weight of non-fermented protein, and preferably there is substantially no (less than 1.0% by weight) fermented protein present in the beverage according to the invention. The protein may preferably be provided as dairy milk, soy milk or rice milk in an amount of 20-80%, more preferably 25-70%, still more preferably 50-70%, and most preferably 40 to 60% by weight of the beverage. The amount of protein is preferably from 0.5 to 5.0%, more preferably from 1.0 to 3.0%, and most preferably from 1.5 to 3.0% by weight of the beverage.

Alternatively the beverage according to the invention contains an amount of protein from 0.75 to 2.5%, preferably from 0.75 to 2.0%, more preferably from 1.0 to 2.0%, still more preferably from 1.5 to 2.0%, and most preferably from 1.2 to 1.8% by weight. These lower levels of proteins are especially suitable in beverages containing non-fermented proteins.

The amount of emulsifier, if present, is preferably from 0.05 to 0.5%, more preferably from 0.1 to 0.4%, and most preferably from 0.1 to 0.3% by weight of the beverage.

The amount of fruit and/or vegetable preparation is preferably from 11.5% to 79.35% by weight, more preferably from 15.0 to 79.35% by weight, still more preferably from 20.0 to 75.0% by weight, even more preferably from 23.5 to 74.25% by weight, further more preferable from 30.0 to 75.0% by weight, still further preferably from 34.4 to 59.25% by weight, and most preferable from 40.0 to 70.0% by weight of the beverage. These amounts include both the added fruit and/or vegetable juice, concentrate, puree or pulp, and the possibly added water, but not the water used for the preparation of the milks if protein powders, isolates or concentrates are used.

The concentration of natural fruit and/or vegetable derived from the fruit and/or vegetable preparation is preferably from 30 to 1000%, more preferably from 40 to 750%, still more preferably 50 to 500%, even more preferably from 80 to 300%, further more preferably from 80 to 250%, and most preferably from 90 to 250% by weight of the beverage.

The beverage according to the invention may alternatively have a concentration of natural fruit and/or vegetable derived from the fruit preparation of at least 101% by weight, preferably from 101 to 1000%, more preferably from 150 to 700%, still more preferably from 170 to 500%, even more preferably from 180 to 300%, and most preferably from 190 to 250% by weight of the beverage.

The amount of stabiliser is preferably from 0.1 to 1.0%, more preferably from 0.2 to 0.8%, and most preferably from 0.2 to 0.6% by weight of the beverage. Preferably the stabiliser comprises pectin, more preferably high methoxy pectin, and most preferably it is substantially (at least 90% by weight) high methoxy pectin.

The beverage according to the invention is homogeneous. This means that it practically comprises particles of a size (volume) of less than 100 μm. Preferably at least 90%, more preferably at least 95%, and most preferably at least 99% of the particles are of a size (volume) less than 100 μm.

Preferably there is no added carbohydrate sweetener in the beverage according to the invention. This means carbohydrate sweeteners are not added to the beverage separately, and not either added to any component included in the beverage. However, the fruit and/or vegetable preparation may contain natural sugars. The beverage according to the invention may further contain at least one non-carbohydrate sweetener.

An example of a preferred beverage composition according to the invention comprises 0.06-5% plant sterol ester and/or plant stanol ester, 0.05-0.5% emulsifier, 0.1-1.0% stabiliser, 25-70% dairy milk, soy milk, rice milk or their mixtures, and 23.5-74.25% fruit and/or vegetable preparation by weight of the beverage. Another preferred example comprises 0.06-5% plant sterol ester and/or plant stanol ester, 0.05-0.5% emulsifier, 0.1-1.0% stabiliser, 40-60% dairy milk, soy milk, rice milk or their mixtures, and 34.4-59.25% fruit and/or vegetable preparation by weight of the beverage. In both these examples the composition is otherwise as disclosed previously in this description; e.g. as preferred aspects. Thus e.g. the concentration of natural fruit and/or vegetable derived from the fruit and/or vegetable preparation is preferably from 30 to 1000%, more preferably from 40 to 750%, still more preferably 50 to 500%, even more preferably from 80 to 300%, further more preferably from 80 to 250%, and most preferably from 90 to 250% by weight of the beverage; or e.g. the concentration of natural fruit and/or vegetable derived from the fruit preparation is at least 101% by weight, preferably from 101 to 1000%, more preferably from 150 to 700%, still more preferably from 170 to 500%, even more preferably from 180 to 300%, and most preferably from 190 to 250% by weight of the beverage; and the stabiliser is high methoxy pectin.

The nutritional value of the beverage according to the invention is improved. A significant part of the daily dose of fruit and/or vegetables can be obtained from the beverage as well as the daily recommended dose of cholesterol lowering plant sterol and/or plant stanol. The beverage contains also nutritious proteins, and if dairy milk is used also calcium. Calcium may preferably also be added to the beverage.

The taste and mouthfeel of the beverage according to the invention are smooth and even. It contains no particles that need to be chewed up. To ensure this the beverage may be homogenised as a final step in the preparation method.

Example 1

Milk Based In-Between Meal Beverage

Comparison of Low Methoxy (LM) and High Methoxy (HM) Pectins

Milk was warmed to 50° C. Melted plant stanol ester and emulsifier was mixed. The milk and the mixture of plant stanol ester and emulsifier was mixed with an Ultra Turrax. Pectin was mixed to hot water (80° C.). The pectin solution was mixed with the berry purees. The milk phase and berry preparation was mixed and homogenised with a two stage homogeniser at 150/50 bar, 50° C. (APV homogeniser Model 1000). The emulsion was treated with UHT (4 s at 144° C., Alfa-Laval Sterilab). The pH value of both the beverages was 4.3.

| Ingredient | Recipe A % | Recipe B % |
| --- | --- | --- |
| Fat free milk, Valio | 50.3 | 50.3 |
| Plant stanol ester, Raisio Nutrition | 2.3 | 2.3 |
| Emulsifier, Datem 1117, Quest | 0.1 | 0.1 |
| LM pectin, Grindstedt SY 200, Danisco | 0.4 | |
| HM pectin Grindstedt AMD 782, Danisco | | 0.4 |
| Blueberry puree, Nordic Jam | 12.0 | 12.0 |

-continued

| Ingredient | Recipe A % | Recipe B % |
|---|---|---|
| Raspberry puree, Nordic Jam | 13.0 | 13.0 |
| Water | 19.6 | 19.6 |

Stability of the products was evaluated directly after cooling, and after 4 and 20 days of storage at refrigerated temperature.

| | Texture evaluation | |
|---|---|---|
| Storage time (days) | Recipe A (LM pectin) | Recipe B (HM pectin) |
| 0 | Milk protein was coagulated; plant stanol ester was homogenously dispersed | Beverage was stable and homogenous and plant stanol ester was well dispersed |
| 4 | Milk protein was coagulated; plant stanol ester was slightly separated (creaming) | Beverage was stable and homogenous and plant stanol ester was well dispersed |
| 20 | Milk protein was coagulated; plant stanol ester was separated (creaming) | Beverage was stable and homogenous and plant stanol ester was well dispersed |

The beverage made using HM pectin had good stability during the whole storage time. In addition to good stability, the beverage had excellent nutritional profile containing 2 g plant stanols, 200 g berries and 2.3 g milk proteins in 150 ml. The beverage had good cholesterol lowering efficacy and contained half of the recommended daily intake of berries. The beverage therefore contained 1.53% by weight of non-fermented dairy milk proteins and the concentration of natural fruit was 133% by weight of the beverage.

Example 2

Milk Based In-Between Meal Beverage

| Ingredient | % |
|---|---|
| Fat free milk, Valio | 50.4 |
| Plant stanol ester, Raisio Nutrition | 1.7 |
| HM pectin Grindstedt AMD 782, Danisco | 0.4 |
| Berry puree mixture, Nordic Jam | 25.0 |
| Water | 22.5 |

Milk was warmed to 50° C. Plant stanol ester was melted. The milk and the plant stanol ester was mixed with an Ultra Turrax. Pectin was mixed to hot water (80° C.). The pectin solution was mixed with the berry puree mixture. The milk phase and berry preparation was mixed and homogenised with a two stage homogeniser at 150/50 bar, 50° C. (APV homogeniser Model 1000). The emulsion was treated with UHT (4 s at 144° C., Alfa-Laval Sterilab).

Stability of the product was evaluated directly after cooling, and after 4 and 20 days of storage at refrigerated temperature. The beverage had good stability during the whole storage time. In addition to good stability, the beverage had excellent nutritional profile containing 1 g plant stanols, 171 g berries and 1.5 g milk proteins in 100 ml. The beverage had good cholesterol lowering efficacy and contained 42% of the recommended daily intake of berries. The beverage therefore contained 1.53% by weight of non-fermented dairy milk proteins and the concentration of natural berries was 171% by weight of the beverage.

Example 3

Soy Milk Based In-Between Meal Beverage

| Ingredient | % |
|---|---|
| Soy milk, Raisio Nutrition (3.0% protein) | 25.0 |
| Plant stanol ester, Raisio Nutrition | 2.3 |
| Diacetyl tartaric acid ester of mono- and diglycerides, Datem 1117, Quest | 0.1 |
| HM pectin Grindsted AMD 782, Danisco | 0.4 |
| Blueberry puree, Nordic Jam | 16.0 |
| Raspberry puree, Nordic Jam | 17.0 |
| Water | 39.2 |

Soy milk was warmed to 50° C. Melted plant stanol ester and emulsifier were mixed. The warmed soy milk and the mixture of plant stanol ester and emulsifier was mixed with an Ultra Turrax. Pectin was mixed with hot water (80° C.) and then mixed with the berry purees. The soy milk preparation and the mixture of berries and pectin was mixed and homogenised with a two stage homogeniser at 150/50 bar 50° C. (APV homogeniser Model 1000). The emulsion was treated with UHT (4 at 144° C., Alfa-Laval Sterilab) and aseptically packed. The pH value was 4.3.

A stable beverage was obtained. Samples were stored at room temperature for 3 months and no creaming was detected.

The beverage contained 0.75% by weight of non-fermented soy protein and the concentration of natural berries was 227% by weight of the beverage.

Example 4

Milk Based In-Between Meal Beverage

| Ingredient | % |
|---|---|
| Fat free milk, Valio | 40.0 |
| Plant stanol ester, Raisio Nutrition | 1.4 |
| Diacetyl tartaric acid ester of mono- and diglycerides, Datem 1117, Quest | 0.1 |
| HM pectin Grindsted AMD 782, Danisco | 0.4 |
| Berry/fruit mixture, concentrate, Kiantama | 35.0 |
| Water | 23.1 |

Milk was warmed to 50° C. Melted plant stanol ester and emulsifier were mixed. The warmed soy milk and the mixture of plant stanol ester and emulsifier was mixed with an Ultra Turrax. Pectin was mixed with hot water (80° C.) and then mixed with the berry/fruit mixture. The milk preparation and the mixture of berries/fruits and pectin was mixed and homogenised with a two stage homogeniser at 150/50 bar 50° C. (APV homogeniser Model 1000). The emulsion was treated with UHT (4 s at 144° C., Alfa-Laval Sterilab) and aseptically packed. The pH value was 4.0.

A stable beverage was obtained.

The beverage contained 1.2% by weight of non-fermented milk protein and the concentration of natural berries was 192% by weight of the beverage.

Example 5

Milk Based In-Between Meal Beverage

| Ingredient | % |
|---|---|
| Fat free milk powder, Valio (32.4% protein) | 2.0 |
| Plant stanol ester, Raisio Nutrition | 3.4 |
| Diacetyl tartaric acid ester of mono- and diglycerides, Datem 1117, Quest | 0.1 |
| HM pectin Grindsted AMD 782, Danisco | 0.4 |
| Berry/fruit mixture, concentrate, Kiantama | 20.0 |
| Orange juice concentrate | 7.0 |
| Sucralose, Splenda | 0.4 |
| Citric acid | 0.2 |
| Water | 66.5 |

Milk powder, pectin, sucralose and berry/fruit mixture were dispersed in water. Plant stanol ester and emulsifier were melted and mixed together. Both phases were warmed to 60° C. and mixed with a blender. The pH was lowered to 3.9 with citric acid. The beverage was homogenised at 250/50 bar 60° C. (APV homogeniser Model 1000), treated with UHT (4 s at 144° C., Alfa-Laval Sterilab) and packed aseptically.

The stability of the beverage was checked for 3 months. No separation of plant stanol ester and no milk coagulation occurred during the storage.

The beverage contained 0.648% by weight of non-fermented dairy milk protein. This corresponds to an amount of 21.7% by weight of milk with a protein content of 3% (as conventional milk) of the beverage. The fruit preparation therefore included 45.5% water obtained from the total added water, 66.5% by weight given in the recipe. The amount of fruit preparation was 72.5% by weight of the beverage (calculated from 20.0% (berry/fruit mixture concentrate)+7.0% (orange juice concentrate)+45.5% (water)) and the concentration of natural fruit was 111% by weight of the beverage.

Example 6

Soy Yoghurt Based Smoothie

| Ingredients | % |
|---|---|
| Soy milk, Raisio Nutrition | 50.2 |
| Plant stanol ester, Raisio Nutrition | 2.6 |
| Citric acid ester of mono/diglycerides, Palsgaard 3203, Palsgaard | 0.2 |
| Glucose, Danisco | 1.1 |
| Sugar, Danisco | 0.4 |
| Corn starch, Cargill | 0.4 |
| Tricalcium phosphate, Gado | 0.2 |
| Salt, Akzo Eka Chemicals | 0.03 |
| Berry/fruit mixture, concentrate, Kiantama | 33.3 |
| HM pectin Grindsted AMD 782, Danisco | 0.2 |
| Water | 11.37 |

Melted plant stanol ester and emulsifier were mixed. Dry ingredients, other than pectin, were mixed with soy milk. The mixture of plant stanol ester and emulsifier was mixed to warm (60° C.) soy milk, the emulsion was warmed to 60° C. and homogenised with a two stage homogeniser at 250/50 bar 60° C. and pasteurised. The emulsion was cooled to 45° C. and a starter culture was added. The product was fermented at 45° C. to a pH level of 4.3 to obtain a yoghurt.

Pectin, berry/fruit mixture, water and yoghurt were mixed together with a blender.

The yoghurt based smoothie was homogenous and stable at refrigerated temperatures for four weeks. The pH of the beverage was 4.2.

Example 7

Yoghurt Based Smoothie

Melted plant stanol ester and emulsifier were mixed. The obtained mixture was mixed to warm (60° C.) milk. The emulsion was warmed to 60° C. and homogenised with a two stage homogeniser at 250/50 bar 60° C. and pasteurised. The emulsion was cooled to 42° C. and a starter culture (Yoghurt V1 PELLET DIP, Danisco) was added. The product was fermented at 42° C. to pH 4.2 to obtain a yoghurt.

Pectin and sugar were dissolved in water and mixed with berry/fruit mixture. The prepared yoghurt was efficiently mixed with the mixture of pectin, sugar and berry/fruit mixture.

| Ingredients | % |
|---|---|
| Fat free milk, Valio | 47.1 |
| Plant sterol ester, Raisio Nutrition | 2.3 |
| Diacetyl tartaric acid ester of mono- and diglycerides, Panodan 165, Danisco | 0.2 |
| Glucose, Danisco | 1.0 |
| Sugar, Danisco | 0.4 |
| HM Pectin, Grindsted AMD 783, Danisco | 0.4 |
| Berry/fruit mixture, concentrate, Kiantama | 33.3 |
| Water | 15.2 |

The texture of the beverage was smooth and the stability of the product was good when stored 2 weeks refrigerated.

The invention claimed is:

1. A beverage comprising protein, plant sterol ester and/or plant stanol ester, a fruit and/or vegetable preparation and a stabiliser, the stabiliser comprising high methoxy pectin in an amount from 0.1 to 1% by weight of the beverage, wherein the beverage has an effective concentration of 30 to 1000% by weight natural fruit and/or vegetable derived from the fruit and/or vegetable preparation, based on the weight of the beverage, and wherein the protein comprises non-fermented protein in an amount of at least 75% by weight of the protein and wherein the ingredients are homogeneously dispersed throughout the beverage.

2. The beverage according to claim 1, wherein an amount of plant sterol ester and/or plant stanol ester is from 0.5 to 7.0% by weight of the beverage.

3. The beverage according to claim 1, wherein the protein comprises non-fermented protein in an amount of at least 99% by weight of the protein.

4. The beverage according to claim 1, wherein the protein is provided as dairy milk, soy milk or rice milk in an amount of from 20 to 80% by weight of the beverage.

5. The beverage according to claim 1, wherein an amount of protein is from 0.5 to 5.0% by weight of the beverage.

6. The beverage according to claim 1, wherein an amount of protein is from 0.75 to 2.5% by weight of the beverage.

7. The beverage according to claim 1, wherein the beverage further comprises an emulsifier in an amount of from 0.05 to 0.5% by weight of the beverage.

8. The beverage according to claim 1, wherein an amount of fruit and/or vegetable preparation is from 11.5% to 79.35% by weight of the beverage.

9. The beverage according to claim 1, wherein the effective concentration of natural fruit and/or vegetable derived from the fruit and/or vegetable preparation is from 40 to 750% by weight of the beverage.

10. The beverage according to claim 1, wherein the effective concentration of natural fruit and/or vegetable derived from the fruit and/or vegetable preparation is at least 101% by weight of the beverage.

11. The beverage according to claim 1, wherein an amount of stabiliser is from 0.2 to 0.8% by weight of the beverage.

12. The beverage according to claim 1, wherein no carbohydrate sweetening agent is added to the beverage.

13. The beverage according to claim 1, wherein the beverage further comprises non-carbohydrate sweetener.

14. A beverage comprising protein, plant sterol ester and/or plant stanol ester, a fruit and/or vegetable preparation, a stabiliser comprising high methoxy pectin, and an emulsifier selected from the group consisting of citric acid ester, lactic acid ester, diacetyl tartaric acid ester of mono- and diglycerides, and mixture thereof in an amount of from 0.05 to 0.5% by weight of the beverage, wherein the beverage has an effective concentration of 30 to 1000% by weight natural fruit and/or vegetable derived from the fruit and/or vegetable preparation, based on the weight of the beverage and wherein the ingredients are homogeneously dispersed throughout the beverage.

15. The beverage according to claim 14, wherein the protein comprises non-fermented protein in an amount of at least 75% by weight of the protein.

16. The beverage according to claim 14, wherein high methoxy pectin is present in an amount from 0.1 to 1% by weight of the beverage.

17. The beverage according to claim 14, wherein an amount of fruit and/or vegetable preparation is from 11.5% to 79.35% by weight of the beverage.

18. The beverage according to claim 14, wherein an amount of plant sterol ester and/or plant stanol ester is from 0.5 to 7.0% by weight of the beverage.

* * * * *